(12) United States Patent
Darveaux et al.

(10) Patent No.: US 8,365,611 B1
(45) Date of Patent: Feb. 5, 2013

(54) BEND TEST METHOD AND APPARATUS FOR FLIP CHIP DEVICES

(75) Inventors: Robert F. Darveaux, Gilbert, AZ (US); Christopher J. Berry, Chandler, AZ (US)

(73) Assignee: Amkor Technology, Inc., Chandler, AZ (US)

( * ) Notice: Subject to any disclaimer, the term of this patent is extended or adjusted under 35 U.S.C. 154(b) by 317 days.

(21) Appl. No.: 12/627,484

(22) Filed: Nov. 30, 2009

(51) Int. Cl.
*G01N 3/32* (2006.01)
*G01N 3/00* (2006.01)
*G01R 31/02* (2006.01)
*G01R 27/28* (2006.01)

(52) U.S. Cl. ......... 73/816; 73/812; 73/849; 324/762.01; 324/762.02; 702/117

(58) Field of Classification Search .................... 73/798, 73/812, 816, 838, 849, 851, 852, 853; 324/762.01–762.03, 763.01, 762.05; 702/117
See application file for complete search history.

(56) References Cited

U.S. PATENT DOCUMENTS

| | | | | |
|---|---|---|---|---|
| 3,323,356 A * | 6/1967 | Arias | ............................. | 73/852 |
| 4,567,774 A * | 2/1986 | Manahan et al. | ............... | 73/849 |
| 5,424,634 A * | 6/1995 | Goldfarb et al. | ................ | 73/798 |
| 5,489,854 A * | 2/1996 | Buck et al. | ............... | 324/762.02 |
| 5,992,242 A * | 11/1999 | Murphy et al. | ................. | 73/840 |
| 6,100,709 A * | 8/2000 | Marieb et al. | ................... | 73/849 |
| 6,747,469 B2 * | 6/2004 | Rutten | .................... | 324/762.03 |
| 7,385,409 B2 * | 6/2008 | Strom | .................... | 324/750.23 |

* cited by examiner

*Primary Examiner* — Lisa Caputo
*Assistant Examiner* — Jonathan Dunlap
(74) *Attorney, Agent, or Firm* — McKay and Hodgson, LLP; Serge J. Hodgson (57) ABSTRACT

A bend test method includes bending a flip chip device into a bent configuration, heating the flip chip device, and inspecting the flip chip device for failure. The bend test method is completed in a relatively short amount of time, e.g., within one to three days. Thus, appropriate failure modes in flip chip devices are created in an accelerated manner so that reliability assessment of various flip chip device designs, materials, and process options can be completed in a few days instead of a few months. This greatly reduced development cycle time typically results in a larger market share for new flip chip device products.

17 Claims, 9 Drawing Sheets

BEND TEST METHOD AND APPARATUS FOR FLIP CHIP DEVICES

BACKGROUND OF THE INVENTION

1. Field of the Invention

The present application relates to the field of electronics, and more particularly, to methods of testing flip chip devices and related test apparatuses.

2. Description of the Related Art

A flip chip device can fail due to underfill delamination and flip chip bump fatigue failures resulting from thermo mechanical stresses in the flip chip device. To avoid these failures in working devices and the associated problems and recalls, a flip chip device design is typically extensively tested to verify the integrity of the flip chip device prior to release of the flip chip device.

Testing typically involves thermal baking or thermal cycling the flip chip device to accelerate the flip chip device failure. Unfortunately, these testing techniques take a significant amount of time, typically on the order of one to three months. This, in turn, delays release of the flip chip device.

SUMMARY OF THE INVENTION

A bend test method includes bending a flip chip device into a bent configuration, heating the flip chip device, and inspecting the flip chip device for failure. The bend test method is completed in a relatively short amount of time, e.g., within one to three days. Thus, appropriate failure modes in flip chip devices are created in an accelerated manner so that reliability assessment of various flip chip device designs, materials, and process options can be completed in a few days instead of a few months. This greatly reduced development cycle time typically results in a larger market share for new flip chip device products.

These and other features of the present invention will be more readily apparent from the detailed description set forth below taken in conjunction with the accompanying drawings.

BRIEF DESCRIPTION OF THE DRAWINGS

In the following description, the same or similar elements are labeled with the same or similar reference numbers.

DETAILED DESCRIPTION

Figure 1:
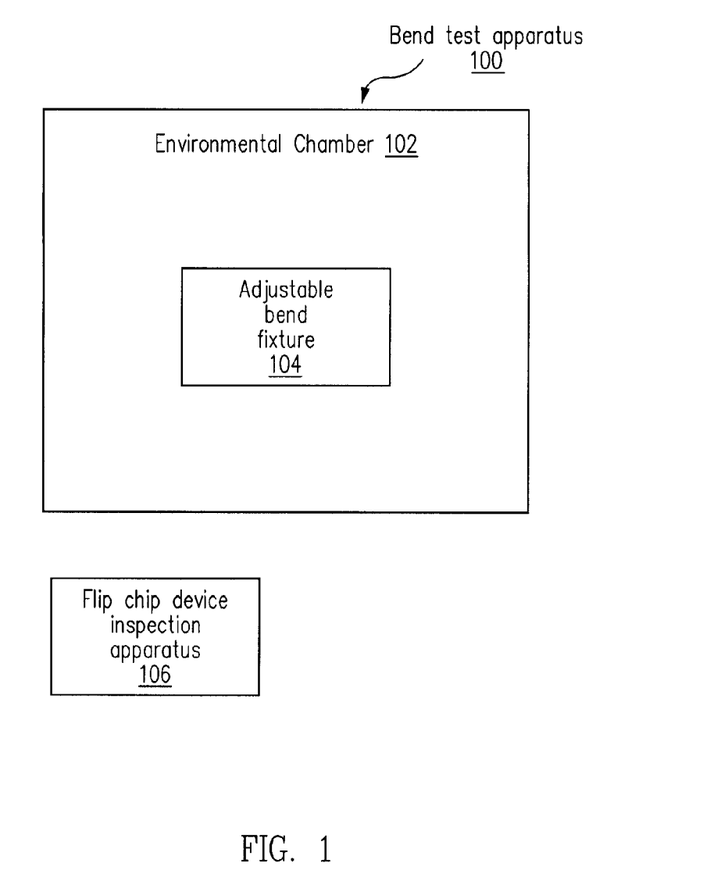
FIG. 1 is a block diagram of a bend test apparatus in accordance with one embodiment.

FIG. 1 is a block diagram of a bend test apparatus 100 in accordance with one embodiment. Bend test apparatus 100 includes an environmental chamber 102, an adjustable bend fixture 104, and a flip chip device inspection apparatus 106.

Environmental chamber 102 is a chamber in which the environment is controlled. Illustratively, the environment within environmental chamber 102 is controlled to have a high temperature, a low temperature, a temperature cycle, although other types of environments such as high humidity environments are provided in other embodiments.

Adjustable bend fixture 104 is located within environmental chamber 102. As discussed in greater detail below, adjustable bend fixture 104 bends a flip chip device being tested. While the flip chip device is bent, the flip chip device is subjected to a thermal bake and/or a thermal cycle using environmental chamber 102.

In one embodiment, a thermal bake, sometimes called a thermal soak, is performed by heating the bent flip chip device to a specific temperature for a specific amount of time. A thermal cycle is performed by heating and cooling the bent flip chip device to specific temperatures within a certain interval of time. Several thermal cycles are performed sequentially in one embodiment.

In one embodiment, cooling means to turn off the heat and allow the bent flip chip device to return to ambient temperature. In another embodiment, cooling means to turn off the heat and to reduce the temperature of the bent flip chip device to below ambient temperature, e.g., using refrigeration, liquid nitrogen, or other cooling technique.

Flip chip device inspection apparatus 106 is an apparatus used to inspect the flip chip device being tested. Illustratively, flip chip device inspection apparatus 106 includes a Scanning Acoustic Microscope (SAM), an electrical test apparatus, an x-ray apparatus, and an Automated Optical Inspection (AOI) apparatus.

As those of skill in the art will understand in light of this disclosure, a scanning acoustic microscope is used to detect voids, cracks, and delamination within a flip chip device using focused sound. An electrical test apparatus measures changes in resistance and open circuits within a flip chip device. An x-ray apparatus, e.g., a 3-D x-ray apparatus, is used to detect voids, cracks, and delamination within a flip chip device using focused x-rays. An automated optical inspection apparatus is used to detect voids, cracks, and delamination within a flip chip device by optical inspection, e.g., of a cross-section of the flip chip device using a Scanning Electron Microscope (SEM). Although several examples are provided, in other embodiments, flip chip device inspection apparatus 106 includes other apparatuses used to inspect flip chip devices.

Figure 2:
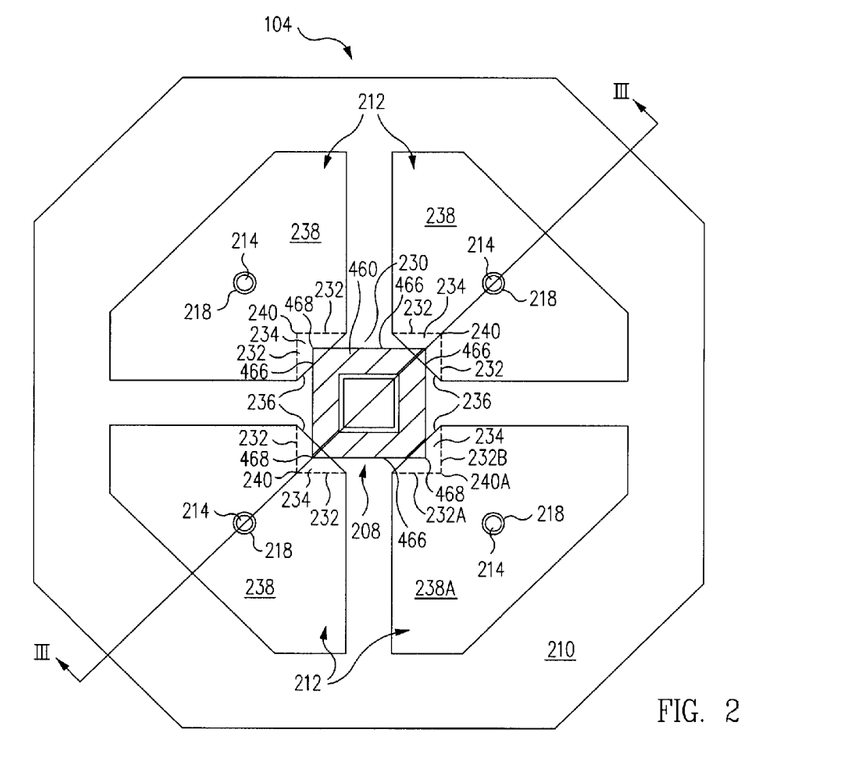
FIG. 2 is a top plan view of an adjustable bend fixture including a flip chip device in accordance with one embodiment.
Figure 3:
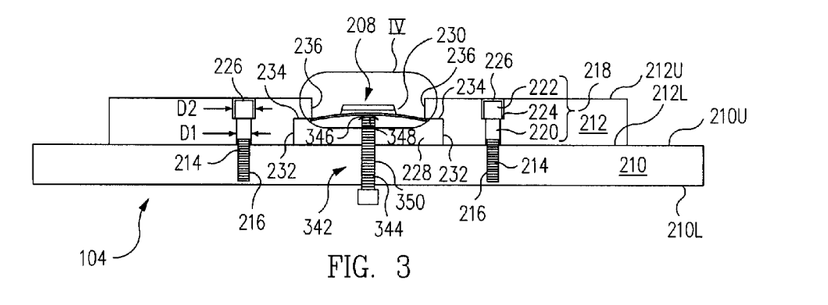
FIG. 3 is a cross-sectional view of the adjustable bend fixture including the flip chip device along the line III-III of FIG. 2 in accordance with one embodiment.
Figure 4:
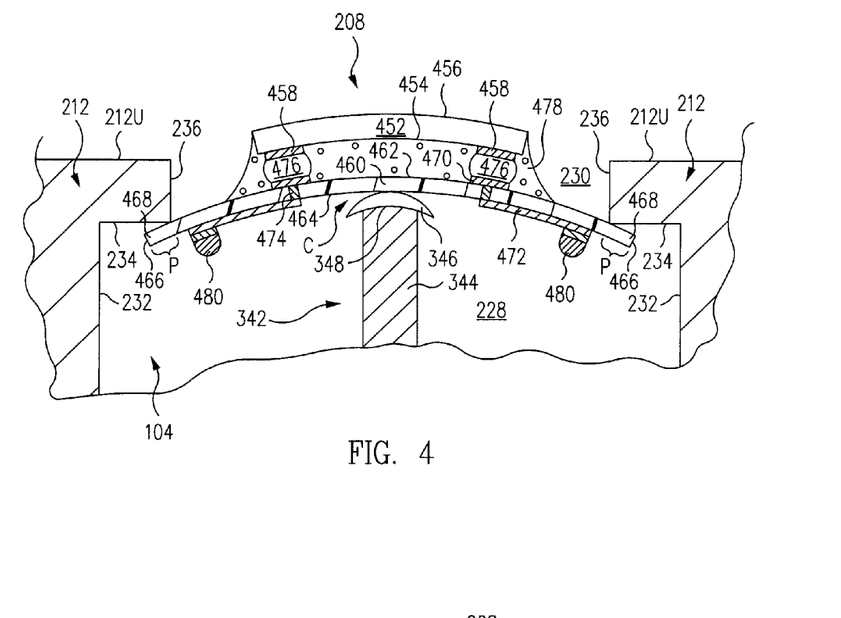
FIG. 4 is an enlarged cross-sectional view of the region IV of the adjustable bend fixture including the flip chip device of FIG. 3.

FIG. 2 is a top plan view of adjustable bend fixture 104 including a flip chip device 208 in accordance with one embodiment. FIG. 3 is a cross-sectional view of adjustable bend fixture 104 including flip chip device 208 along the line III-III of FIG. 2 in accordance with one embodiment. FIG. 4 is an enlarged cross-sectional view of the region IV of adjustable bend fixture 104 including flip chip device 208 of FIG. 3.

Referring now to FIGS. 2, 3, and 4 together, adjustable bend fixture 104 includes a base plate 210 and a clamp plate 212 mounted thereto. More particularly, base plate 210 includes an upper, e.g., first, surface 210U and clamp plate 212 includes a lower, e.g., first, surface 212L. Lower surface 212L of clamp plate 212 is mounted to upper surface 210U of base plate 210.

In accordance with this embodiment, clamp plate 212 is mounted to base plate 210 by threaded screws 214. Illustratively, base plate 210 includes threaded apertures 216 extending downward from upper surface 210U. Clamp plate 212 includes screw apertures 218 extending entirely through clamp plate 212 from an upper, e.g., second, surface 212U of clamp plate 212 to lower surface 212L of clamp plate 212.

Screw apertures 218 have a first diameters D1 at lower sections 220 of screw apertures 218 extending from lower surface 212L. Screw apertures 218 further have second diameters D2 at upper sections 222 of screw apertures 218 extending from upper surface 212U. Screw apertures 218 further include shoulders 224 at the intersections of lower sections 220 and upper sections 222.

Shoulders 224 are circular annuluses perpendicular to screw apertures 218 and parallel to upper surface 210U of base plate 210, upper surface 212U of clamp plate 212 and lower surface 212L of clamp plate 212. Although various features may be described herein as being parallel, perpendicular, or having other relationships, in light of this disclosure, those of skill in the art will understand that the features may not be exactly parallel, perpendicular, but only substantially parallel, perpendicular, to within excepted manufacturing tolerances.

To mount clamp plate 212 to base plate 210, screws 214 are passed through screw apertures 218 in clamp plate 212 and threaded into threaded apertures 216 of base plate 210. Screws 214 including enlarged screw heads 226 that press downwards against shoulders 224 thus pressing clamp plate 212 downward into base plate 210.

As described above, clamp plate 212 is mounted to base plate 210 using screws 214 as fasteners. However, in other embodiments, other fasteners such as clamps, snaps, clasps, or other fasteners are used. Generally, the fasteners allow clamp plate 212 to be readily attached and detached from base plate 210.

Clamp plate 212 defines a flip chip device cavity 228 and a flip chip device opening 230. More particularly, flip chip device cavity 228 is defined by upper surface 210U of base plate 210, flip chip device cavity sidewalls 232 of clamp plate 212, and flip chip device shelves 234 of clamp plate 212.

Flip chip device cavity sidewalls 232 extend perpendicularly from lower surface 212L of clamp plate 212 and thus perpendicularly upwards from upper surface 210U of base plate 210. Flip chip device shelves 234 extend perpendicularly inwards from flip chip device cavity sidewalls 232 to flip chip device opening sidewalls 236 of clamp plate 212.

Flip chip device opening sidewalls 236 extend perpendicularly upwards between flip chip device shelves 234 and upper surface 212U of clamp plate 212. Flip chip device opening sidewalls 236 define flip chip device opening 230. As illustrated, flip chip device opening 230 extends through clamp plate 212 to expose flip chip device cavity 228.

In accordance with this embodiment, clamp plate 212 includes four separate quarter plates 238. Each quarter plate 238 is fastened to base plate 210 using one or more screws 214 as discussed above.

As indicated by the dashed lines, each quarter plate 238 includes a first flip chip device cavity sidewall 232 perpendicular to a second flip chip device cavity sidewall 232. The intersection of flip chip device cavity sidewalls 232 defining corners 240 of flip chip device cavity 228.

To illustrate, a first quarter plate 238A of the plurality of quarter plates 238 includes a first flip chip device cavity sidewall 232A and a second flip chip device cavity sidewall 232B of the plurality of flip chip device cavity sidewalls 232. Flip chip device cavity sidewall 232A is perpendicular to flip chip device cavity sidewall 232B. The intersection of flip chip device cavity sidewalls 232A, 232B define a first corner 240A of the plurality of corners 240.

Each quarter plate 238 includes a flip chip device shelf 234. Flip chip device shelf 234 is shaped as a right triangle in accordance with this embodiment. More particularly, corner 240 is a right angle, i.e., a 90° angle. The intersection of flip chip device cavity sidewalls 232 and flip chip device shelf 234 defines legs of the right triangle. Finally, the intersection of flip chip device opening sidewall 236 and flip chip device shelf 234 defined the hypotenuse of the right triangle. Although a right triangle is set forth, in other embodiments, flip chip devices shelves 234 have other shapes. In one particular embodiment, corners 240 are greater than 90° angles, e.g., are 110° angles.

Further, in accordance with this embodiment, adjustable bend fixture 104 further includes a bending actuator 342. In accordance with this embodiment, bending actuator 342 includes a threaded screw 344.

Optionally, a cushioning pad 346 is mounted on an upper end 348 of threaded screw 344. Cushioning pad 346 provides a cushion thus distributing the force from upper end 348 of screw 344.

In accordance with this embodiment, base plate 210 further includes a bending actuator threaded aperture 350 extending entirely through base plate 210 and between a lower, e.g., second, surface 210L of base plate 210 and upper surface 210U. Threaded screw 344 is threaded into threaded aperture 350. Accordingly, rotation of threaded screw 344 moves upper end 348 and cushioning pad 346 upwards and downwards relative to base plate 210 and clamp plate 212.

Flip chip device 208 includes an electronic component 452. Electronic component 452 is an integrated circuit chip, e.g., an active component. However, in other embodiments, electronic component 452 is a passive component such as a capacitor, resistor, or inductor.

In accordance with this embodiment, electronic component 452 includes an active surface 454 and an opposite inactive surface 456. Electronic component 452 further includes bond pads 458 formed on active surface 454.

Flip chip device 208 further includes a substrate 460 including a first surface 462 and an opposite second surface 464. Substrate 460 further includes sides 466 extending perpendicularly between first surface 462 and second surface 464. The periphery of first surface 462 and second surface 464 is the region of first surface 462 and second surface 464, respectively, directly adjacent sides 466. Sides 466 intersect at corners 468 of substrate 460.

Substrate 460 further includes a first circuit pattern 470 on first surface 462 and a second circuit pattern 472 on second surface 464. Circuit pattern 470 is electrically connected to circuit pattern 472 through substrate 460, e.g., by electrically conductive vias 474.

Bond pads 458 are flip chip mounted to first circuit pattern 470, e.g., lands thereof, by flip chip bumps 476, e.g., solder bumps. An underfill 478 is applied between active surface 454 of electronic component 452 and first surface 462 of substrate 460 and around flip chip bumps 476. Optionally, interconnection balls 480, e.g., solder, are formed on second circuit pattern 472, e.g., lands thereof.

Although one example of flip chip device 208 is provided above and illustrated in the figures, in light of this disclosure, those of skill in the art will understand that flip chip device 208 is representative of any one of a number of different flip chip devices that can be tested using bend test apparatus 100 in accordance with various embodiments. For example, additional electronic components are stacked upon electronic component 452 to form a stacked flip chip device in other embodiments. Further, additional devices such as passive devices are mounted to substrate 460 to form an integrated passive flip chip device in other embodiments.

Flip chip device 208 is loaded into adjustable bend fixture 104 such that clamp plate 212 contacts the periphery P of first surface 462 of substrate 460 only. Bending actuator 342 presses upwards on the center C of second surface 464 of substrate 460. This forces periphery P upwards against clamp plate 212 thus holding flip chip device 208 in place.

More particularly, flip chip device cavity 228 is larger than flip chip device 208 allowing flip chip device 208 to be located within flip chip device cavity 228. In one embodiment, flip chip device cavity 228 allows a wide variety of different size flip chip devices to be fit therein allowing the same adjustable bend fixture 104 to be used with the wide variety of different size flip chip devices.

Flip chip device shelves 234 extend inwards and over corners 468 of flip chip device 208. Accordingly, flip chip device shelves 234 contacts periphery P of first surface 462 of substrate 460 at corners 468. For simplicity, it is sometimes said that clamp plate 212 holds four corners 468 of flip chip device 208.

It is to be understood that the portion of substrate 460 outward of flip chip device opening sidewalls 236 would be covered by clamp plate 212 and thus would not be visible in the view of FIG. 2. The entirety of substrate 460 is illustrated in FIG. 2 to facilitate understanding of the principles in accordance with this embodiment.

Electronic component 452 protrudes upwards and into flip chip device opening 230. Bending actuator 342, e.g., upper end 348 including cushioning pad 346, contacts and presses upwards on center C of second surface 464 of substrate 460.

Accordingly, clamp plate 212 applies downward force to periphery P of substrate 460. Conversely, bending actuator 342 applies an equal but opposite upward force to center C of substrate 460. By forcing periphery P of substrate 460 downward and center C of substrate 460 upward, a bending force is applied to substrate 460 and thus to flip chip device 208. This bending force bends flip chip device 208.

As illustrated in FIG. 4, flip chip device 208 is bent in a concave direction. As used herein, the direction of bending of flip chip device 208 is relative to second surface 464 of substrate 460 opposite first surface 462 of substrate 460 to which electronic component 452 is flip chip mounted.

Paying particular attention once again to FIG. 2, as set forth above, clamp plate 212 includes four separate quarter plates 238. Each quarter plate 238 is fastened to base plate 210 using one or more screws 214 as discussed above.

In accordance with one embodiment, to load flip chip device 208 into adjustable bend fixture 104, one or more of quarter plates 238 are unscrewed from base plate 210 and removed. Flip chip device 208 is then positioned above base plate 210 and bending actuator 342. The removed quarter plates 238 are then screwed back to base plate 210 thus locating flip chip device 208 within flip chip device cavity 228 of clamp plate 212.

Bending actuator 342 is then activated, e.g., by screwing threaded screw 344 into base plate 210 to move upper end 348 and cushioning pad 346 upwards. This moves upper end 348 and cushioning pad 346 into center C of flip chip device 208 thus moving flip chip device 208 into contact with clamp plate 212. Threaded screw 344 is rotated until the desired force is applied to flip chip device 208 providing the desired degree of bending of flip chip device 208. Flip chip device 208 is removed from adjustable bend fixture 104 by reversing the above operations.

Figure 5:
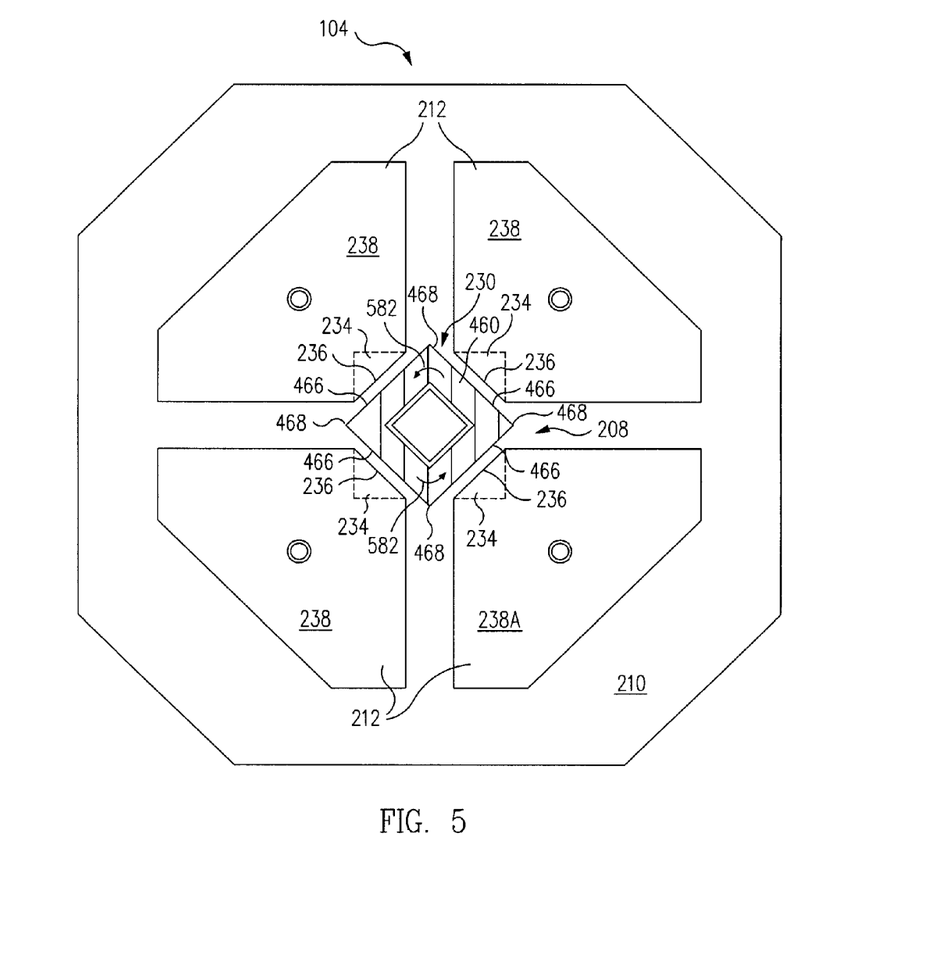
FIG. 5 is a top plan view of the adjustable bend fixture during loading of the flip chip device in accordance with one embodiment.

As discussed below in reference to FIG. 5, in another embodiment, flip chip device 208 is loaded into adjustable bend fixture 104 without removal of clamp plate 212, e.g., quarter plates 238, from base plate 210. FIG. 5 is a top plan view of adjustable bend fixture 104 during loading of flip chip device 208 in accordance with this embodiment.

Referring now to FIGS. 3, 4, and 5 together, in accordance with this embodiment, the distance between flip chip device opening sidewalls 236 is greater than the width of flip chip device 208. This allows flip chip device 208 to be inserted into and through flip chip device opening 230 between flip chip device opening sidewalls 236 as illustrated in FIG. 5.

Once passed through flip chip device opening 230, flip chip device 208 is rotated as indicated by the arrows 582. This rotation of flip chip device 208 moves corners 468 under flip chip device shelves 234 of clamp plate 212.

Bending actuator 342 is then activated, e.g., by screwing threaded screw 344 into base plate 210 to move upper end 348 and cushioning pad 346 upwards. This moves upper end 348 and cushioning pad 346 into center C of flip chip device 208 thus moving flip chip device 208 into contact with clamp plate 212. Threaded screw 344 is rotated until the desired force is applied to flip chip device 208 providing the desired degree of bending of flip chip device 208. Flip chip device 208 is removed from adjustable bend fixture 104 by reversing the above operations.

Although clamp plate 212 is set forth as including four quarter plates 238, in other embodiments, clamp plate 212 is integral, i.e., is formed of a single piece and not a plurality of separate pieces connected together or includes two or three separate plates.

Figure 6:
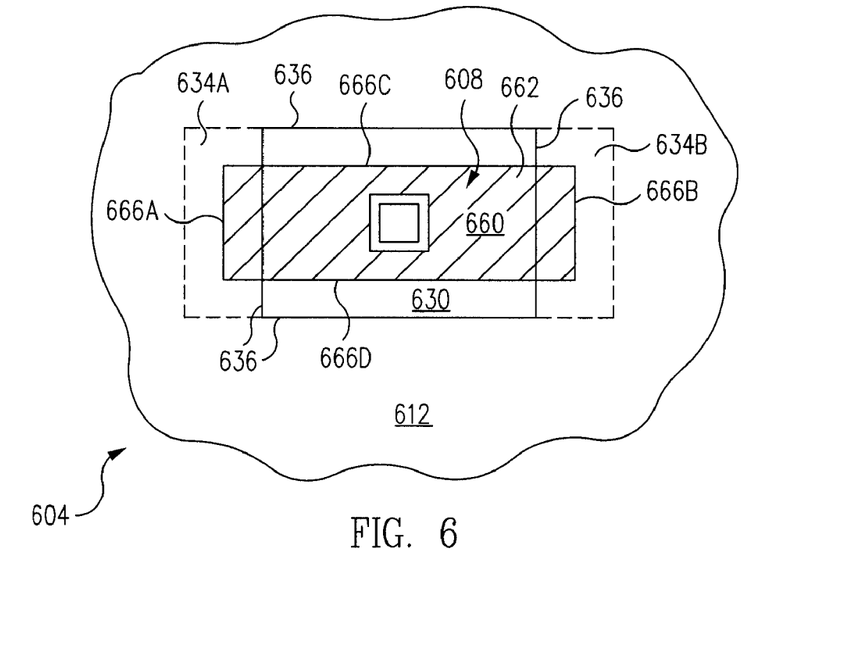
FIG. 6 is a top plan view of a region of an adjustable bend fixture including a flip chip device in accordance with another embodiment.

FIG. 6 is a top plan view of a region of an adjustable bend fixture 604 including a flip chip device 608 in accordance with another embodiment. In accordance with this embodiment, a clamp plate 612 includes a flip chip device opening 630 defined by flip device opening sidewalls 636. Further, clamp plate 612 includes flip chip device shelves 634A, 634B opposite one another. Flip chip device shelves 634A, 634B are indicated by the dashed lines for purposes of illustration although it is to be understood that flip chip device shelves 634A, 634B would not be visible in the view of FIG. 6.

In accordance with this embodiment, flip chip device 608 is rectangular having a longer width than length. More particularly, flip chip device 608 includes short sides 666A, 666B opposite one another and long sides 666C, 666D also opposite one another. Long sides 666C, 666D are longer than short sides 666A, 666B.

In accordance with this embodiment, clamp plate 612 contacts and presses downwards on the periphery of a first surface 662 of a substrate 660 of flip chip device 608 adjacent short sides 666A, 666B. More particularly, flip chip device shelves 634A, 634B contact first surface 662 of substrate 660 adjacent short sides 666A, 666B. For simplicity, it is sometimes said that clamp plate 612 holds two sides, i.e., short sides 666A, 666B, of flip chip device 608.

It is to be understood that the portion of substrate 660 outward of flip chip device opening sidewalls 636 would be covered by clamp plate 612 and thus would not be visible in the view of FIG. 6. The entirety of substrate 660 is illustrated in FIG. 6 to facilitate understanding of the principles in accordance with this embodiment.

In contrast, long sides 666C, 666D are unrestrained by clamp plate 612. More particularly, the distance between long sides 666C, 666D is less than the distance between the respective flip chip device opening sidewalls 636 allowing long sides 666C, 666D to fit within flip chip device opening 630.

In the above manner, downward force is applied to two opposite sides of flip chip device 608 only. Although restraining of short sides 666A, 666B is set forth, in another embodiment, only long sides 666C, 666D are restrained by clamp plate 612 in a similar manner. In yet another embodiment, flip chip device 608 is square, i.e., has four equal sides, and only two opposite sides of the square flip chip device 608 are restrained by clamp plate 612. In yet another embodiment at set forth below in reference to FIG. 7, all four sides are restrained.

Figure 7:
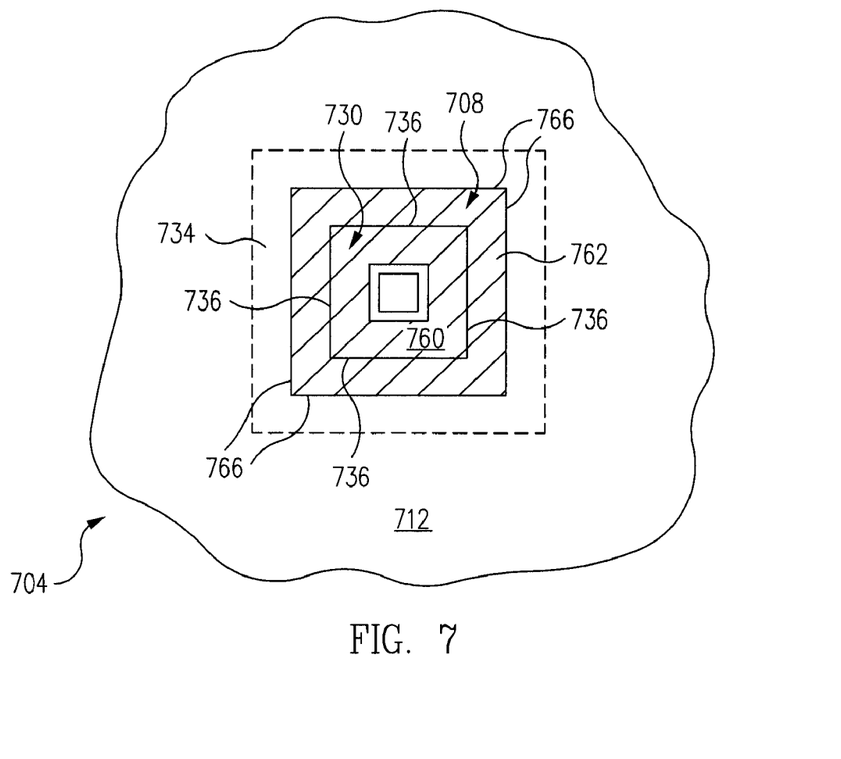
FIG. 7 is a top plan view of a region of an adjustable bend fixture including a flip chip device in accordance with yet another embodiment.

FIG. 7 is a top plan view of a region of an adjustable bend fixture 704 including a flip chip device 708 in accordance with yet another embodiment. In accordance with this embodiment, a clamp plate 712 includes a flip chip device opening 730 defined by flip device opening sidewalls 736. Further, clamp plate 712 includes a flip chip device shelf 734 entirely surrounding flip chip device opening 730. Flip chip device shelf 734 is indicated by the dashed line for purposes of illustration although it is to be understood that flip chip device shelf 734 would not be visible in the view of FIG. 7.

In accordance with this embodiment, flip chip device 708 is square having four equal sides 766. Clamp plate 712 contacts and presses downwards on the periphery of a first surface 762 of a substrate 760 of flip chip device 708 adjacent all four sides 766. More particularly, flip chip device shelf 734 contacts first surface 762 of substrate 760 adjacent all four sides 766. For simplicity, it is sometimes said that clamp plate 712 holds all four sides 766 of flip chip device 708.

It is to be understood that the portion of substrate 760 outward of flip chip device opening sidewalls 736 would be covered by clamp plate 712 and thus would not be visible in the view of FIG. 7. The entirety of substrate 760 is illustrated in FIG. 7 to facilitate understanding of the principles in accordance with this embodiment.

In the above manner, downward force is applied to all four sides 766 of flip chip device 708.

Figure 8:
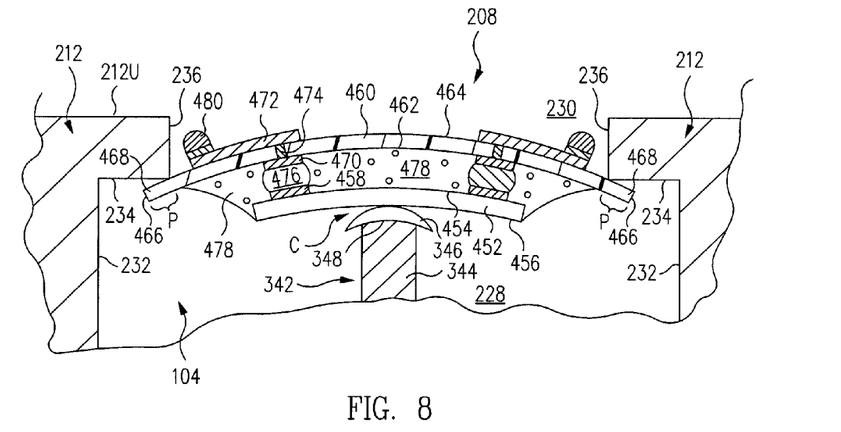
FIG. 8 is an enlarged cross-sectional view of the adjustable bend fixture including the flip chip device of FIG. 4 in accordance with another embodiment.

FIG. 8 is enlarged cross-sectional view of adjustable bend fixture 104 including flip chip device 208 of FIG. 4 in accordance with another embodiment. FIG. 8 is similar to FIG. 4 with the exception being that flip chip device 208 is inverted compared with the view of FIG. 4.

More particularly, referring now to FIG. 8, flip chip device shelves 234 extend inwards and over corners 468 of flip chip device 208. Accordingly, flip chip device shelves 234 contacts periphery P of second surface 464 of substrate 460 at corners 468. Substrate 460 protrudes upwards and into flip chip device opening 230. Bending actuator 342, e.g., upper end 348 including cushioning pad 346, contact inactive surface 456 of electronic component 452.

Accordingly, clamp plate 212 applies downward force to periphery P of substrate 460. Conversely, bending actuator 342 applies an equal but opposite upward force to electronic component 452. By forcing periphery P of substrate 460 downward and electronic component 452 upward, a bending force is applied to flip chip device 208. This bending force bends flip chip device 208 in a convex direction as illustrated in FIG. 8.

Figure 9:
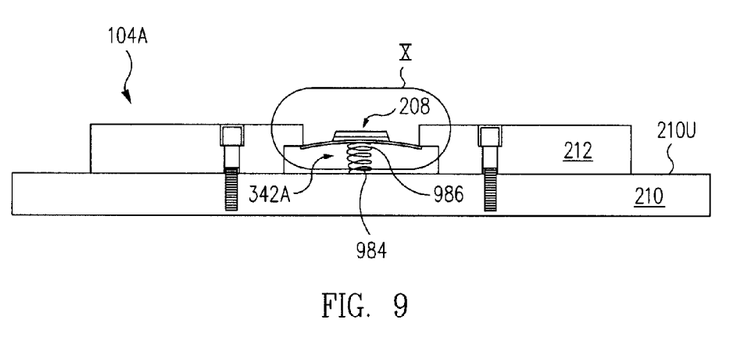
FIG. 9 is a cross-sectional view of an adjustable bend fixture including a flip chip device in accordance with another embodiment.
Figure 10:
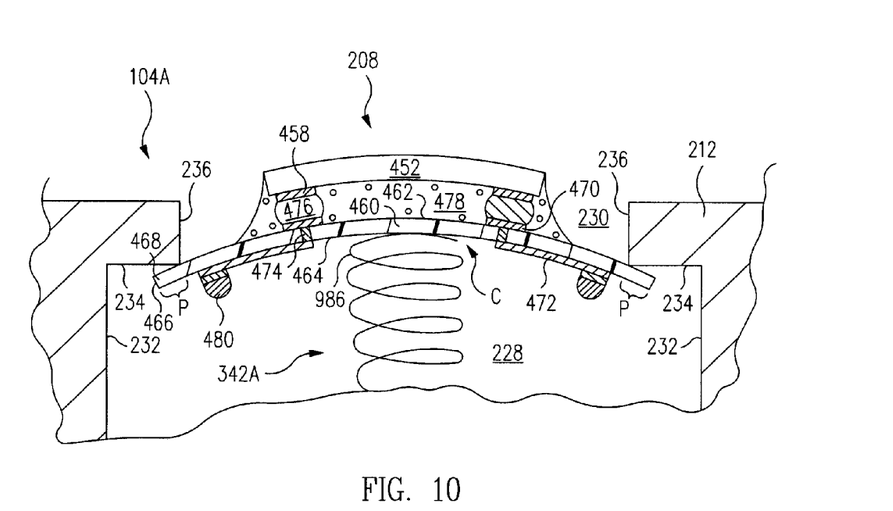
FIG. 10 is an enlarged cross-sectional view of the region X of the adjustable bend fixture including the flip chip device of FIG. 9.

FIG. 9 is a cross-sectional view of an adjustable bend fixture 104A including flip chip device 208 in accordance with another embodiment. FIG. 10 is an enlarged cross-sectional view of the region X of adjustable bend fixture 104A including flip chip device 208 of FIG. 9. Adjustable bend fixture 104A of FIGS. 9, 10 is substantially similar to adjustable bend fixture 104 of FIGS. 3, 4 and only the significant differences between adjustable bend fixtures 104A, 104 are discussed below.

Referring now to FIGS. 9 and 10 together, adjustable bend fixture 104A includes a bending actuator 342A. In accordance with this embodiment, bending actuator 342A includes a spring having a lower, e.g., first, end 984 and upper, e.g., second, end 986.

Lower end 984 contacts upper surface 210U of base plate 210. In one embodiment, lower end 984 is secured to upper surface 210U of base plate 210 thus securing bending actuator 342A to base plate 210.

Upper end 986 contacts center C of second surface 464 of substrate 460 of flip chip device 208. Bending actuator 342A is compressed between upper surface 210U of base plate 210 and center C of second surface 464 of substrate 460 of flip chip device 208. Due to this compression, bending actuator 342A, e.g., upper end 986 presses upwards on center C of second surface 464 of substrate 460. Accordingly, bending actuator 342 is located between flip chip device 208 and base plate 210. In one embodiment, bending actuator 342A is not permanently attached to base plate 210 but mechanically floats and is fixed in position by virtue of the spring force applied between flip chip device 208 and base plate 210.

As those of skill in the art will understand in light of this disclosure, by knowing the spring constant of bending actuator 342A and the displacement of upper end 986 from its equilibrium position, the force applied to center C of second surface 464 of substrate 460 by bending actuator 342A is readily calculated. Examples of suitable forces include 9 Newtons (N) and 42N. While several examples of useful bending forces are cited herein, in light of this disclosure, those of skill in the art will understand that virtually any bending force can be applied subject to the specific flip chip device being tested and the particular dimensions of the adjustable bend fixture.

As discussed above, clamp plate 212 applies downward force to periphery P of substrate 460. Conversely, bending actuator 342A applies an equal but opposite upward force to center C of substrate 460. By forcing periphery P of substrate 460 downward and center C of substrate 460 upward, a bending force is applied to substrate 460 and thus to flip chip device 208. This bending force bends flip chip device 208 in a concave direction as illustrated in FIGS. 9 and 10.

Although not illustrated in the other embodiments, in light of this disclosure, those of skill in the art will understand that bending actuator 342A of FIGS. 9, 10, e.g., a spring, can be used in any of the other embodiments in place of bending actuator 342, e.g., a threaded screw.

Figure 11:
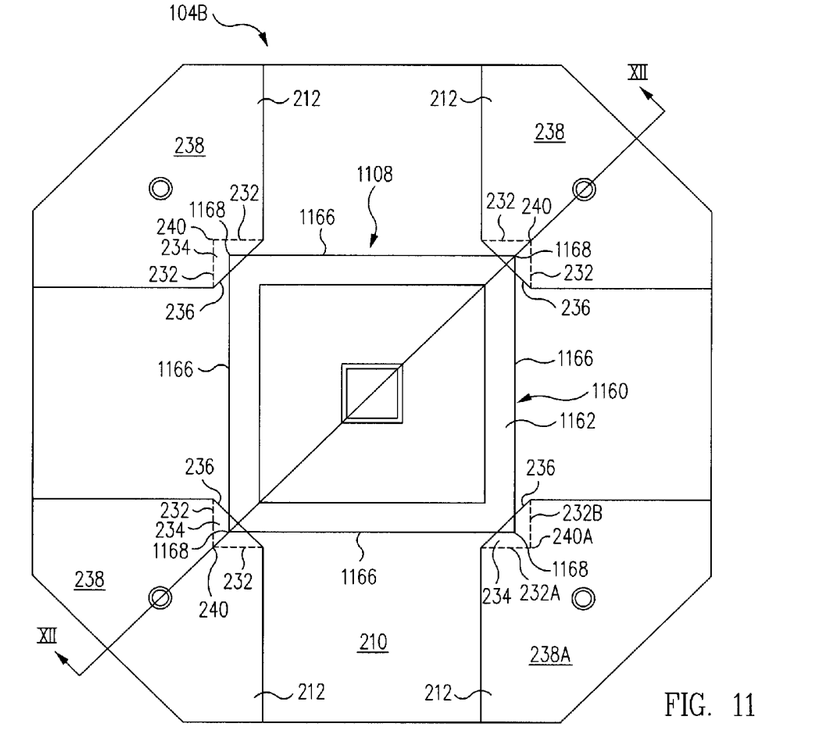
FIG. 11 is a top plan view of an adjustable bend fixture including a flip chip device in accordance with one embodiment.
Figure 12:
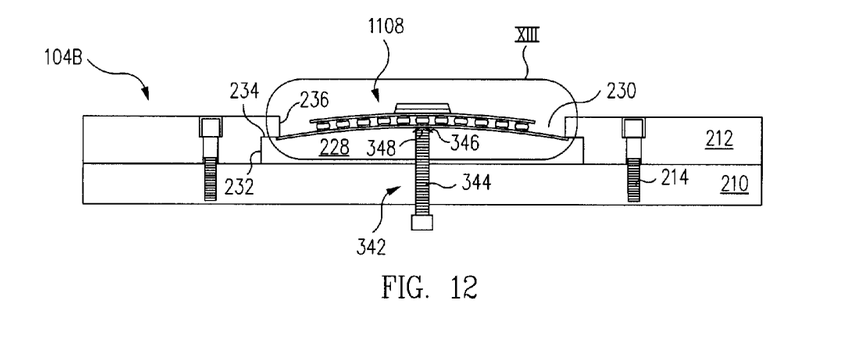
FIG. 12 is a cross-sectional view of the adjustable bend fixture including the flip chip device along the line XII-XII of FIG. 11 in accordance with one embodiment.
Figure 13:
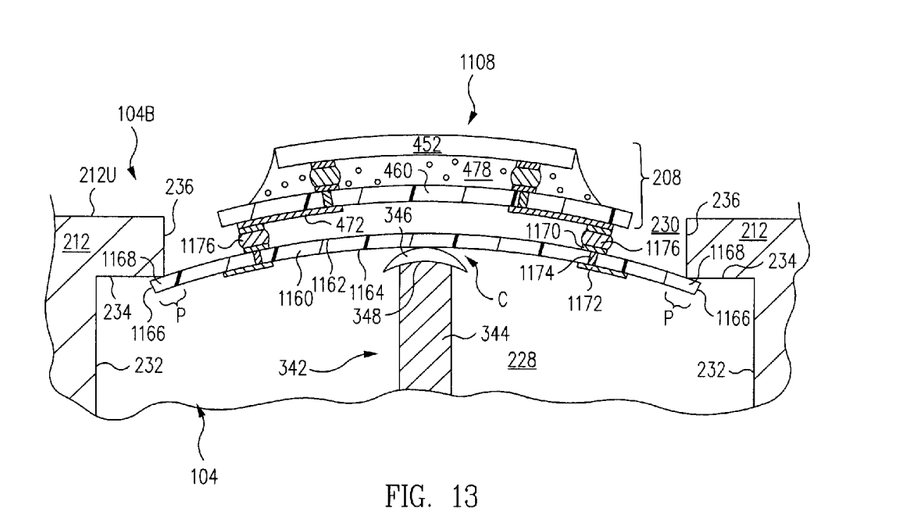
FIG. 13 is an enlarged cross-sectional view of the region XIII of the adjustable bend fixture including the flip chip device of FIG. 12.

FIG. 11 is a top plan view of an adjustable bend fixture 104B including a flip chip device 1108 in accordance with one embodiment. FIG. 12 is a cross-sectional view of adjustable bend fixture 104B including flip chip device 1108 along the line XII-XII of FIG. 11 in accordance with one embodiment. FIG. 13 is an enlarged cross-sectional view of the region XIII of adjustable bend fixture 104B including flip chip device 1108 of FIG. 12.

Flip chip device 1108 is loaded, bent, and unloaded from adjustable bend fixture 104B in a manner similar to loading, bending, and unloading, of flip chip device 208 from adjustable bend fixture 104 as discussed above in reference to FIGS. 2, 3, and 4. Some significant differences between flip chip device 1108, adjustable bend fixture 104B of FIGS. 11, 12, 13 and flip chip device 208, adjustable bend fixture 104 of FIGS. 2, 3, 4 are discussed below.

Referring now to FIGS. 11, 12, and 13 together, in accordance with this embodiment, flip chip device 1108 includes flip chip device 208 as described above. Flip chip device 208 is referred to as a flip chip package 208 in accordance with this embodiment. Flip chip device 1108 further includes a substrate 1160, e.g., a printed circuit motherboard, to which flip chip package 208 is mounted.

Substrate 1160 includes a first surface 1162 and an opposite second surface 1164. Substrate 1160 further includes sides 1166 extending perpendicularly between first surface 1162 and second surface 1164. The periphery of first surface 1162 and second surface 1164 is the region of first surface 1162 and second surface 1164, respectively, directly adjacent sides 1166. Sides 1166 intersect at corners 1168 of substrate 1160.

Substrate 1160 further includes a first circuit pattern 1170 on first surface 1162 and a second circuit pattern 1172 on second surface 1164. Circuit pattern 1170 is electrically connected to circuit pattern 1172 through substrate 1160, e.g., by electrically conductive vias 1174.

Second circuit pattern 472, e.g., lands thereof, of flip chip package 208 are mounted to first circuit pattern 1170, e.g., lands thereof, by interconnection bumps 1176, e.g., solder bumps. In one embodiment, interconnection balls 1176 are formed by reflowing interconnection balls 480 (interconnection balls 480 are illustrated in FIG. 4).

Although one example of flip chip device 1108 having flip chip package 208 mounted to substrate 1160, e.g., a printed circuit mother board, is provided above and illustrated in the figures, in light of this disclosure, those of skill in the art will understand that flip chip device 1108 is representative of any one of a number of different flip chip devices that can be tested using bend test apparatus 100 in accordance with this embodiment.

Flip chip device 1108 is loaded into adjustable bend fixture 104B such that clamp plate 212 contacts the periphery P of first surface 1162 of substrate 1160 only. Bending actuator 342 presses upwards on the center C of second surface 1164 of substrate 1160. This forces periphery P upwards against clamp plate 212 thus holding flip chip device 1108 in place.

More particularly, flip chip device cavity 228 is larger than flip chip device 1108 allowing flip chip device 1108 to be located within flip chip device cavity 228. In one embodiment, flip chip device cavity 228 allows a wide variety of different sized flip chip devices to be fit therein allowing the same adjustable bend fixture 104B to be used with the wide variety of different sized flip chip devices.

Flip chip device shelves 234 extend inwards and over corners 1168 of flip chip device 1108. Accordingly, flip chip device shelves 234 contacts periphery P of first surface 1162 of substrate 1160 at corners 1168. For simplicity, it is sometimes said that clamp plate 212 holds four corners 1168 of flip chip device 1108. However, in other embodiments, two or more of sides 1166 of substrate 1160 are held by clamp plate 212 in a manner similar to that discussed above regarding FIGS. 6, 7.

It is to be understood that the portion of substrate 1160 outward of flip chip device opening sidewalls 236 would be covered by clamp plate 212 and thus would not be visible in the view of FIG. 11. The entirety of substrate 1160 is illustrated in FIG. 11 to facilitate understanding of the principles in accordance with this embodiment.

Flip chip package 208 protrudes upwards and into flip chip device opening 230. Bending actuator 342, e.g., upper end 348 including cushioning pad 346, contacts and presses upwards on center C of second surface 1164 of substrate 1160.

Accordingly, clamp plate 212 applies downward force to periphery P of substrate 1160. Conversely, bending actuator 342 applies an equal but opposite upward force to center C of substrate 1160. By forcing periphery P of substrate 1160 downward and center C of substrate 1160 upward, a bending force is applied to substrate 1160 and thus to flip chip device 1108. This bending force bends flip chip device 1108 in the concave direction as illustrated in FIGS. 12 and 13.

Figure 14:
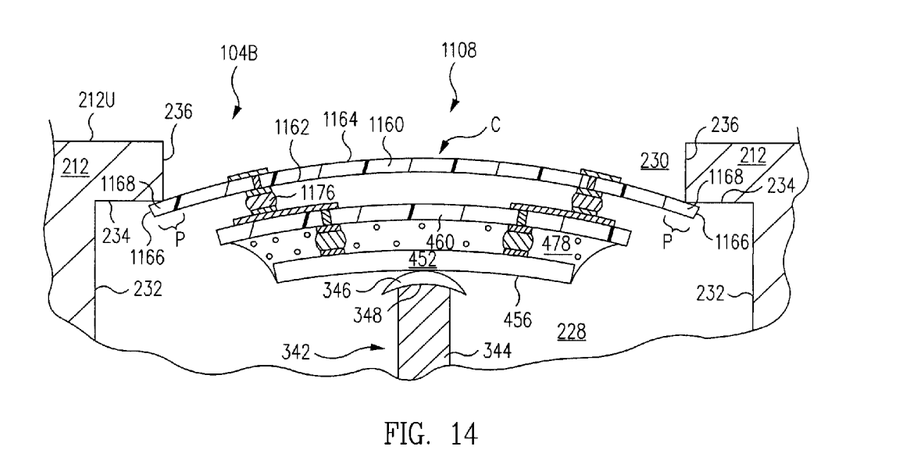
FIG. 14 is an enlarged cross-sectional view of the adjustable bend fixture including the flip chip device of FIG. 13 in accordance with another embodiment.

FIG. 14 is an enlarged cross-sectional view of adjustable bend fixture 104B including flip chip device 1108 of FIG. 13 in accordance with another embodiment. FIG. 14 is similar to FIG. 13 with the exception being that flip chip device 1108 is inverted compared with the view of FIG. 13.

More particularly, referring now to FIG. 14, flip chip device shelves 234 extend inwards and over corners 1168 of flip chip device 1108. Accordingly, flip chip device shelves 234 contact periphery P of second surface 1164 of substrate 1160 at corners 1168. Substrate 1160 protrudes upwards and into flip chip device opening 230. Bending actuator 342, e.g., upper end 348 including cushioning pad 346, contact inactive surface 456 of electronic component 452 although directly contact first surface 1162 of substrate 1160 in other embodiments.

Accordingly, clamp plate 212 applies downward force to periphery P of substrate 1160. Conversely, bending actuator 342 applies an equal but opposite upward force to electronic component 452 and generally to center C of substrate 1160. By forcing periphery P of substrate 1160 downward and center C of substrate 1160 upward, a bending force is applied to flip chip device 1108. This bending force bends flip chip device 1108 in a convex direction as illustrated in FIG. 14.

Figure 15:
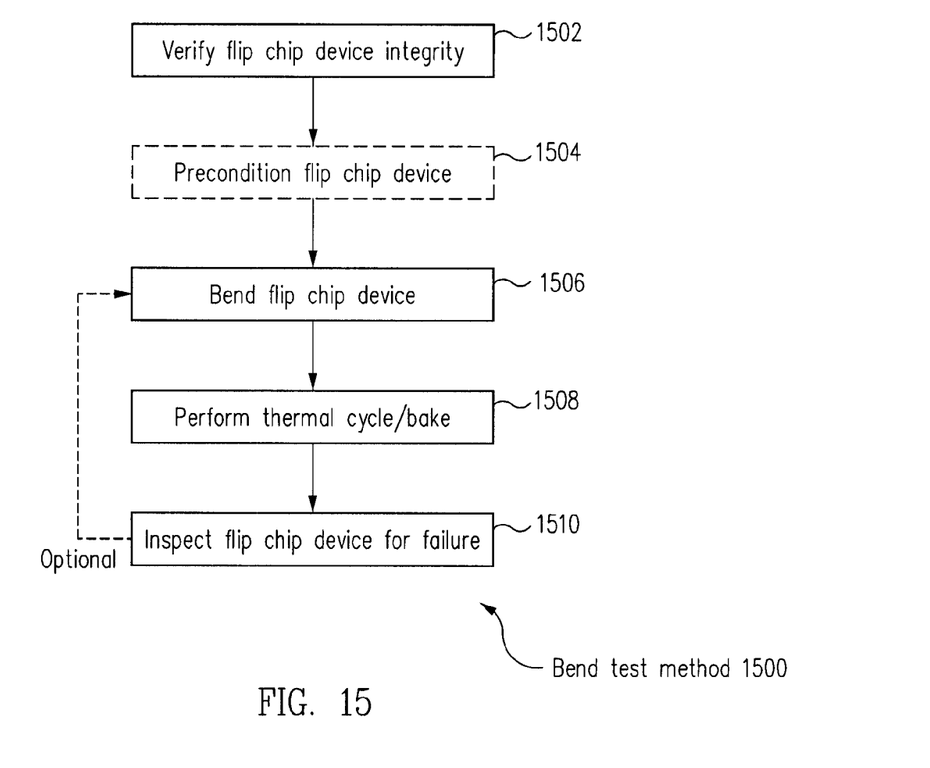
FIG. 15 is a block diagram of a bend test method in accordance with one embodiment.

FIG. 15 is a block diagram of a bend test method 1500 in accordance with one embodiment. Referring now to FIGS. 1, 2, 3, 4 and 15 together, in a verify flip chip device integrity operation 1502, the integrity of flip chip device 208 is verified. Illustratively, flip chip device inspection apparatus 106 is used to verify that bumps 476 electrically connecting bond pads 458 to first circuit pattern 470 are not cracked or malformed. Further, underfill 478 is inspected to verify an absence of voids and delamination.

From verify flip chip device integrity operation 1502, flow moves, optionally, to a precondition flip chip device operation 1504. In precondition flip chip device operation 1504, flip chip device 208 is preconditioned. In one embodiment, flip chip device 208 is dried to remove all moisture from flip chip device 208 or placed under vacuum to remove all residual gases. In another embodiment, flip chip device 208 is thermally baked at a set relative humidity. For example, flip chip device 208 is thermally baked for 8 hours at 85° C. and then is thermally baked for 16 hours at 85° C. with 85% relative humidity (RH). Although various examples of preconditioning are provided, in light of this disclosure, it is understood that flip chip device 208 can be preconditioned using other techniques.

From precondition flip chip device operation 1504 (or directly from verify flip chip device integrity operation 1502 in the event that precondition flip chip device operation 1504 is not performed), flow moves to a bend flip chip device operation 1506. In bend flip chip device operation 1506, flip chip device 208 is bent using adjustable bend fixture 104 as discussed above.

From bend flip chip device operation 1506, flow moves to a perform thermal cycle/bake operation 1508. In perform thermal cycle/bake operation 1508, flip chip device 208 in its bent configuration is subjected to a thermal cycle/bake, i.e., heated.

Illustratively, adjustable bend fixture 104 including flip chip device 208 in its bent configuration are placed within environmental chamber 102. A thermal cycle/bake is then performed using environment chamber 102.

In one example, a 9N or 42N force is applied by bending actuator 342. A thermal cycle of 0° C. to 100° C., 1 cycle per hour, for 63 cycles is performed.

In another example, a 54N force is applied by bending actuator 342. A thermal cycle of 0° C. to 125° C., 1 cycle per hour, for 25 cycles is performed.

In another example, a 54N force is applied by bending actuator 342. A thermal bake of 125° C. for six hours is performed.

From perform thermal cycle/bake operation 1508, flow moves to an inspect flip chip device for failure operation 1510. In inspect flip chip device for failure operation 1510, flip chip device 208 is inspected for failure. Illustratively, flip chip device inspection apparatus 106 is used to verify that bumps 476 electrically connecting bond pads 458 to first circuit pattern 470 are not cracked, fractured, or otherwise malformed. Further, underfill 478 is inspected to verify an absence of voids and delamination.

In one embodiment, flip chip device 208 is removed from environmental chamber 102 and adjustable bend fixture 104 and inspected for failure.

In another embodiment, changes in electrical properties, e.g., resistance and open circuits, within flip chip device 208 are measured to determine whether there has been a failure within flip chip device 208. These changes in electrical properties are monitored in real-time during performance of perform thermal cycle/bake operation 1508 in one embodiment. In another embodiment, these changes in electrical properties are monitored after performance of perform thermal cycle/bake operation 1508.

In one embodiment, upon completion of inspect flip chip device for failure operation 1510, a determination is made whether flip chip device 208 failed or passed bend test method 1500. In another embodiment, upon verifying that flip chip device 208 did not fail, operations 1506, 1508, and 1510 are repeated as indicated by the optional arrow at the left.

In one example, a 11N force is applied by bending actuator 342 in bend flip chip device operation 1506. A thermal bake of 125° C. for six hours is performed in perform thermal cycle/bake operation 1508. The flip chip device is inspected in inspect flip chip device for failure operation 1510.

Returning again to bend flip chip device operation 1506, a 26N force is applied by bending actuator 342. A thermal bake of 125° C. for six hours is again performed in perform thermal cycle/bake operation 1508. The flip chip device is again inspected in inspect flip chip device for failure operation 1510.

Returning again to bend flip chip device operation 1506, a 39N force is applied by bending actuator 342. A thermal bake of 125° C. for six hours is again performed in perform thermal cycle/bake operation 1508. The flip chip device is finally inspected in inspect flip chip device for failure operation 1510.

In one embodiment, bend test method 1500 is completed in a relatively short amount of time, e.g., within one to three days. Thus, using bend test apparatus 1500, appropriate failure modes in a flip chip device are created in an accelerated manner so that reliability assessment of various flip chip device designs, materials, and process options can be completed in a few days instead of a few months. This greatly reduced development cycle time typically results in a larger market share for new flip chip device products.

Although bend test method 1500 is described relative to flip chip device 208 and adjustable bend fixture 104 of FIGS. 2, 3, 4, in light of this disclosure, those of skill in the art will understand that bend test method 1500 is equally applicable to any of the other adjustable bend fixtures and flip chip devices as described herein.

The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. A bend test method comprising:
    inserting a flip chip device through a flip chip device opening in a clamp plate;
    rotating the flip chip device to move corners of the flip chip device under triangular flip chip device shelves of the clamp plate;
    bending the flip chip device into a bent configuration, the flip chip device comprising an electronic component flip chip mounted to a substrate;
    heating the flip chip device; and
    inspecting the flip chip device for failure.

2. The bend test method of claim 1 wherein the bending comprising:
    applying a first force to a periphery of the flip chip device; and
    applying an equal and opposite second force to a center of the flip chip device.

3. The bend test method of claim 2 wherein an adjustable bend fixture for performing the bending comprises:
    the clamp plate that applies the first force; and
    a bending actuator that applies the second force.

4. The bend test method of claim 3 wherein the clamp plate holds four corners of the flip chip device.

5. The bend test method of claim 1 wherein the flip chip device is bent in a concave direction.

6. The bend test method of claim 1 further comprising verifying an integrity of the flip chip device prior to the bending.

7. The bend test method of claim 1 further comprising preconditioning the flip chip device.

8. The bend test method of claim 1 wherein the heating comprises performing a thermal bake of the flip chip device.

9. The bend test method of claim 1 wherein the heating comprises performing a thermal cycle on the flip chip device.

10. The bend test method of claim 1 wherein the bending, heating, and inspecting are repeatedly performed.

11. The bend test method of claim 1 wherein the bend test takes one to three days to complete.

12. A bend test apparatus comprising:
  a base plate;
  a clamp plate defining a flip chip device cavity configured to have a flip chip device located therein and a flip chip device opening configured to allow the flip chip device to be passed therethrough, the flip chip device comprising an electronic component flip chip mounted to a substrate, the clamp plate being attached to the base plate, wherein the clamp plate comprises triangular flip chip device shelves;
  a bending actuator contacting the base plate.

13. The bend test apparatus of claim 12 wherein the clamp plate further comprises:
  a lower surface;
  flip chip device cavity sidewalls extending from the lower surface, wherein the flip chip device shelves extend from the flip chip device cavity sidewalls;
  an upper surface; and
  flip chip opening sidewalls extending from the flip chip device shelves to the upper surface.

14. A bend test apparatus for testing a flip chip device comprising:
  a clamp plate comprising triangular flip chip device shelves contacting a periphery of the flip chip device, the flip chip device comprising an electronic component flip chip mounted to a substrate; and
  a bending actuator contacting a center of the flip chip device.

15. The bend test apparatus of claim 14 wherein the clamp plate applies a first force to the periphery of the flip chip device; and
  wherein the bending actuator applies an equal and opposite second force to the center of the flip chip device thus bending the flip chip device.

16. The bend test apparatus of claim 14 further comprising an environmental chamber for heating the flip chip device.

17. The bend test apparatus of claim 14 further comprising a flip chip device inspection apparatus for inspecting the flip chip device.

* * * * *